United States Patent [19]
Cottman

[11] 3,984,372
[45] Oct. 5, 1976

[54] POLYMER COMPOSITIONS CONTAINING ESTERS OF POLYPHENOLIC COMPOUNDS AS BUILT-IN ANTIOXIDANTS

[75] Inventor: Kirkwood S. Cottman, Akron, Ohio

[73] Assignee: The Goodyear Tire & Rubber Company, Akron, Ohio

[22] Filed: July 25, 1975

[21] Appl. No.: 599,296

Related U.S. Application Data

[62] Division of Ser. No. 467,426, May 6, 1974, abandoned.

[52] U.S. Cl. .................. 260/47 UA; 260/45.85 E; 260/45.95 R
[51] Int. Cl.² ............... C08F 19/00; C08F 15/02; C08F 7/02; C08G 33/10
[58] Field of Search ................................. 260/47 UA

[56] References Cited

UNITED STATES PATENTS

| | | | |
|---|---|---|---|
| 3,305,522 | 2/1967 | Spacht | 260/45.95 H |
| 3,457,328 | 7/1969 | Blatz et al. | 260/47 UA |
| 3,625,874 | 12/1971 | Cottman et al. | 260/5 |
| 3,629,197 | 12/1971 | Stiehl | 260/47 UA |
| 3,645,970 | 2/1972 | Kleiner | 260/47 UA |

*Primary Examiner*—Joseph L. Schofer
*Assistant Examiner*—Herbert J. Lilling
*Attorney, Agent, or Firm*—F. W. Brunner; J. A. Rozmajzl

[57] ABSTRACT

This invention concerns a method for the preparation of polyphenolic esters for use as built-in antioxidants.

9 Claims, No Drawings

POLYMER COMPOSITIONS CONTAINING ESTERS OF POLYPHENOLIC COMPOUNDS AS BUILT-IN ANTIOXIDANTS

This is a division of application Ser. No. 467,426 filed May 6, 1974, now abandoned.

This invention relates to new polyphenolic type antioxidants, to a method of preparing the materials and to polymer compositions concerning these materials.

The prior art teaches that antioxidant activity in phenolic compounds occurs because of hydrogen abstraction from the hydroxyl groups [Scott "Atmospheric Oxidation and Antioxidants" Chapter IV, 1965]. It has been found according to the present invention that by partial esterification of a polyphenolic compound, both antioxidant activity and nonstaining characteristics can be enhanced. This is a surprising result since it appears to contradict the prior art theory on how phenolic antioxidants perform.

It is an object of the present invention to provide new polymerizable phenolic ester antioxidants and a process for their manufacture. Further objects will be evident to those skilled in this art as the description proceeds.

The antioxidants of this invention are partial esters of polyphenols. The term "partial esters" is used to mean esterified polyphenols in which less than all of the phenolic hydroxyl groups of the phenol are esterified.

The above compounds are prepared by reacting (A) polyphenolic compounds containing two or more aromatic rings which each contain phenolic hydroxyl groups with (B) acid halides or other similar derivatives capable of forming unsaturated polymerizable esters. The polyphenolic starting materials may be initially prepared by methods well known to those skilled in this art or it may be a commercially available polyphenolic. A description of the preparation of some of these polyphenolic compounds can be found in U.S. Pat. Nos. 3,036,138 and 3,305,522.

Polyphenolic compounds which can be used to prepare the antioxidants of this invention have the structural formula

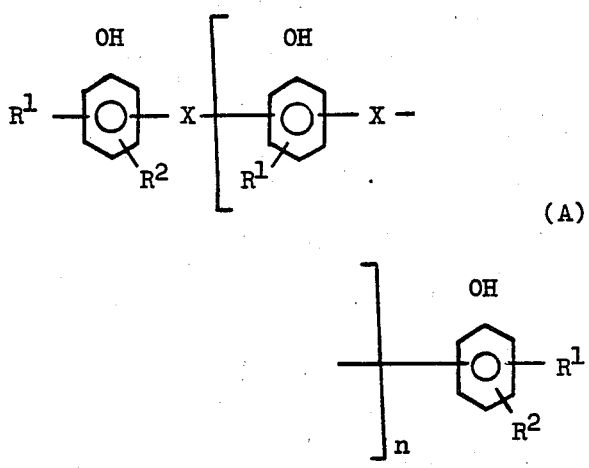

(A)

wherein $R^1$ and $R^2$ are the same or different radicals selected from the group consisting of hydrogen and alkyl radicals containing from 1 to 16 carbon atoms, cycloalkyl radicals containing from 5 to 9 carbon atoms, aralkyl radicals containing from 7 to 12 carbon atoms, and substituted and unsubstituted aryl radicals having from 6 to 12 carbon atoms and $R^1$ preferably contains from 1 to 2 carbon atoms when para to the hydroxyl group, X is the same or different radical selected from the group consisting of (1) cyclic dienes with non-adjacent carbon to carbon double bonds within the ring structure containing from 5 to 20 carbon atoms from which the divalent radicals are prepared and (2) a bivalent radical selected from the group consisting of —S—, —O—, —C=O, —CH$_2$—, —S—S— and wherein $n$ is selected from the group consisting of 0 and real numbers from 1 to 5.

The polyphenolic is reacted with a compound capable of forming an ester having the general formula

(B)

wherein $R^3$ is selected from the group consisting of hydrogen and alkyl radicals having from 1 to 4 carbon atoms, $R^4$ is selected from the group consisting of hydrogen, alkyl radicals having from 1 to 4 carbon atoms, aralkyl radicals having from 7 to 12 carbon atoms, cycloalkyl radicals having from 5 to 8 carbon atoms and substituted or unsubstituted aryl radicals having from 6 to 12 carbon atoms, and wherein A is selected from the group consisting of chlorine, bromine and iodine. The amount of esterification of course depends on the molar ratios and steric hindrance of the materials used. Preferably the polyphenolic material is treated with from one mole to 0.1 mole of ester forming compound for each functional hydroxyl group. More preferably at least one functional hydroxyl group per polyphenolic molecule is esterified.

When the polyphenolics and ester forming compounds described herein are reacted in a 1:1 molar ratio, a near theoretical reaction takes place. Compounds having the formula (A) wherein $n$ is 0 and X is a divalent radical selected from the group consisting of —S—, —CH$_2$—, and $R^2$ is a hydrocarbon radical of at least 4 carbon atoms (preferably tertiary) and ortho to the hydroxyl group, have only one readily reactive hydroxyl group. Upon esterification of one hydroxyl group, steric hindrance operates to decrease the reaction at the second hydroxyl site. For example, if one mole of methacryloyl chloride is reacted with one mole of 2,2'-methylene-bis-(4-methyl-6-tert.butylphenol) a near theoretical amount of 2-(2-hydroxy-3-tert.butyl-5-methylbenzyl)-4-methylphenyl methacrylate is obtained.

When a polyphenolic according to structure (A) wherein $R^2$ (preferably tertiary) is ortho to the hydroxyl group and is reacted with $n + 2$ moles of an ester forming compound having structure (B), less than $n + 2$ mols of compound (B) will react. Normally the number of ester groups reacting with the polyphenolic reactant is not more than $n + 1.5$ or less than $n - 0.75$. When $n$ is 0 the number of ester groups reacting with the polyphenolic is usually not more than 1.5 or less than 0.25.

The esterification reaction may easily take place at elevated pressure and temperatures from 0° to the boiling point of the reactants. Preferably temperatures from 0° to 60° C. are preferred.

Representative examples of the radicals of the above formulas are alkyl radicals such as methyl, ethyl, butyl, pentyl, hexyl and decyl; cycloalkyl radicals such as cyclopentyl, cyclohexyl; alkylaryl radicals such as methylphenyl and decylphenyl; aryl radicals such as phenyl and naphthyl; aralkyl radicals such as benzyl and 4-methylbenzyl; and halogens such as bromo, iodo and chloro.

The above compounds are prepared by reacting conventional antioxidant compounds comprising polyphenolic compounds having 2 or more aromatic rings containing phenolic hydroxyl groups with compounds such acryloyl chloride or other similar derivatives capable of forming unsaturated polymerizable esters. Some of the polyphenolic starting materials can be initially prepared by methods well known to those skilled in this art such as those taught in U.S. Pat. Nos. 3,305,522 and 3,036,138. The phenolic esters of this invention may be chemically bonded or "built" onto polymer chains. Such built-in antioxidants can not be lost due to volatility or extraction.

Representative examples of cyclic dienes useful in this invention are 1,5-cyclooctadiene, cyclopentadiene, bicyclo[2.2.1]-2,5-heptadiene, 2-methyl bicyclo[2.2.1]-2,5-heptadiene, dicyclopentadiene, pentacyclo [8.2.1.1$^{4,7}$.0$^{2,9}$.0$^{3,8}$]-tetradeca-5,11-diene, and 1,5,9-cyclodedecadiene.

Representative examples of phenolic compounds useful in the practice of this invention include 2,6-bis-(2-hydroxy-3-tert.butyl-5-methylbenzyl)-4-methylphenol; 2,2'-methylene-bis-(4-methyl-6-tert.butylphenol); 2,2'-methylene-bis-(4-ethyl-6-tert.butylphenol); 2,2'-thio-bis-(4-methyl-6-tert.butylphenol); 2-(3,5-ditert.butyl-4-hydroxybenzyl)-4-methylphenol; 4-(3,5-ditert.butyl-4-hydroxybenzyl)phenol; 2-(3,5-ditert.butyl-4-hydroxybenzyl)phenol; 2-(3,5-ditert.butyl-4-hydroxybenzyl)-5-methylphenol and 2,6-bis-(2-hydroxy-3-tert.butyl-5-ethylbenzyl)-4-ethylphenol, and compounds similar to those prepared in U.S. Pat. Nos. 3,625,874; 3,036,138 and 3,305,522.

Representative examples of ester forming compounds that can be used in the practice of this invention include acryloyl chloride, methacryloyl chloride, crotonyl chloride, cinnamoyl chloride, acryloyl bromide, ethacryloyl chloride, β-cyclohexyl acryloyl chloride and β-(4-methylcyclohexyl)acryloyl chloride.

Representative examples of compounds produced by the process of the present invention are listed below.

2-(2-hydroxy-3-tert.butyl-5-methylbenzyl)-4-methyl-6-tert.butylphenyl acrylate 2-(2-hydroxy-3-tert.butyl-5-methylbenzyl)-4-methyl-6-tert.butyl phenylmethacrylate 2-(3,5-ditert.butyl-4-hydroxybenzyl)-4-methylphenyl methacrylate 2-(3,5-ditert.butyl-4-hydroxybenzyl)-4-methylphenyl acrylate 4-(3,5-ditert.butyl-4-hydroxybenzyl) phenyl acrylate 2-(2-hydroxy-3-tert.butyl-5-methylphenylthio)-4-methyl-6-tert.butyl phenyl methacrylate 2-(3,5-ditert.butyl-4-hydroxybenzyl) phenyl methacrylate 2,6-bis(2-hydroxy-3-tert.butyl-5-methylbenzyl)-4-methylphenyl methacrylate and the reaction products of Examples 3 through 7, 9 and 10.

The polyphenolic compounds described in this invention can be reacted with the ester forming compounds in a ratio as described above. Preferably at least one mole of ester forming compound is reacted with one mole of polyphenolic compound.

The polymers that may be conveniently protected by the compounds described herein are vulcanized and unvulcanized polymers susceptible to oxygen degradation, such as natural rubber, balata, gutta percha and rubbery synthetic polymers containing carbon to carbon double bonds. Representative examples of the synthetic polymers used in the practice of this invention are polychloroprene; homopolymers of a conjugated 1,3-diene such as isoprene and butadiene with up to 40 percent by weight of at last one copolymerizable monomer such as styrene and acrylonitrile; butyl rubber, which is a polymerization product of a major proportion of a monoolefin and a minor proportion of a multiolefin such as butadiene or isoprene; polyurethanes containing carbon to carbon double bonds; and polymers and copolymers of monoolefins containing little or no unsaturation, such as polyethylene, polypropylene, ethylene propylene copolymers and terpolymers of ethylene, propylene and a nonconjugated diene. When added in free form normally 0.001 to 10.0 precent of the antioxidant by weight based on the weight of the polymer can be used, although the precise amount of the age resisters which is to be employed will depend somewhat on the nature of the polymer and the severity of the deteriorating conditions to which the polymer is to be exposed. In unsaturated polymers such as those made from conjugated dienes, the amount of age resister necessary is greater than that required by a saturated polymer such as polyethylene. It has been found that an effective antioxidant amount of the disclosed stabilizers in rubbery unsaturated polymers will generally range from 0.05 to 5.0 percent by weight based on the weight of the polymer although it is commonly preferred to use from 0.5 to 3.0 percent by weight based on the weight of the polymer. Mixtures of the age resisters may be used. These polymers, whether liquid or solid, have a special advantage in that the antioxidant portion is not extractable, and therefore the polymeric compositions are highly resistant to oxidative aging even after repeated exposure to aqueous detergent solutions or drycleaning fluids. This feature is especially significant where polymers are used in foam backings for rugs and where polymers are used in solution or latex form to treat fabrics, since such products are often exposed to aqueous detergent solutions or drycleaning fluids.

A polymer composition will usually contain other compounding materials such as additives and reinforcing materials used with vulcanized rubber products. Representative examples of such additives are metal oxides, reinforcing agents, pigments, fillers, softening agents, other antioxidants, plasticizing agents, curing agents and the like.

The examples below illustrate typical runs made to produce the polyphenolic ester antioxidant. All parts and percentages are by weight unless otherwise indicated.

EXAMPLE 1

Three hundred and twenty-four grams of p-cresol and 5.3 grams of BF$_3$ etherate were added to a flask equipped with a water condenser, stirrer, thermometer and heated to 90° C. One hundred thirty-two grams of dicyclopentadiene were added over a 20 minute period. Five grams of lime were then added and the reaction product was heated to a reactor temperature of 195° C. at 20 millimeters of mercury. Three hundred grams of toluene were added and the product was filtered. The toluene was removed from the product at a reaction temperature of 180°C. under vacuum. The reaction product had a weight of 300 grams.

EXAMPLE 2

One hundred grams of the polyphenolic product prepared in Example 1 and 10 grams of toluene sulfonic acid were dissolved in 100 milliliters of toluene between 60° C. and 70° C. Isobutylene was added until no more would react. The reaction was neutralized with 10 grams of $Na_2CO_3$ in aqueous solution, then decanted. The reaction product was heated to a reactor temperature of 170° C. under vacuum to remove volatiles in the presence of one gram of dry sodium carbonate. The reaction product had a weight of 122 grams.

EXAMPLE 3

One hundred grams of the butylated polyphenol prepared in Example 2, 8.9 grams of triethylamine and 150 milliliters of tetrahydrofuran were heated to 65° C. 4.4 Grams of methacryloyl chloride were added to the reaction product. The reaction product was stirred for 90 minutes between 65° C. and 70° C. and then filtered. The reaction products of butylated polyphenol/¼ mole methacryloyl chloride was heated to a reactor temperature of 165° C. at 25 millimeters of mercury to remove the volatiles.

EXAMPLE 4

This example was carried out in the same manner as Example 3 using 100 grams of the butylated polyphenol prepared as described in Example 2. 17.9 Grams of triethylamine and 8.8 grams of methacryloyl chloride were used yielding the reaction product of one mole butylated polyphenol/½ mole methacryloyl chloride.

EXAMPLE 5

Fifty grams of the product prepared as described in Example 2 were dissolved in 50 milliliters of tetrahydrofuran and 17.7 grams of triethylamine at 70° C. 8.8 Grams of methacryloyl chloride were added. The mixture was stirred at 70° C. for 3½ hours and then filtered. The reaction product of one mole butylated polyphenol/one mole methacryloyl chloride was heated to a reactor temperature of 160° C. at 15 millimeters of mercury to remove volatiles.

EXAMPLE 6

This example was carried out in the same manner as Example 3 using 100 grams of the butylated polyphenol prepared as described in Example 2. 35.2 Grams of methacryloyl chloride and 71 grams of triethylamine were used yielding the reaction product of one mole butylated polyphenol/2 moles methacryloyl chloride. The reaction product had a weight of 128 grams.

EXAMPLE 7

This example was carried out in the same manner as Example 3 using 100 grams of the butylated polyphenol prepared as described in Example 2. 107 Grams of triethylamine and 52.8 grams of methacryloyl chloride were used yielding the reaction product of one mole butylated polyphenol/3 mole methacryloyl chloride.

EXAMPLE 8

Nine hundred seventy-two grams of p-cresol and 16 grams of $BF_3$ etherate were heated to 90° C. 396 Grams of dicyclopentadiene were added over a 30 minute period. Seventy-five grams of triethyl phosphite and 15 grams of calcium hydroxide were then added. The mixture were stirred at 95° C. for 2 hours and then the unreacted p-cresol was removed at a reactor temperature of 205° C. and 15 millimeters of mercury. The resin was diluted with 500 milliliters of toluene and filtered. The filtrate was heated to remove the toluene solvent yielding the product having a weight of 909 grams.

EXAMPLE 9

This example was carried out in the same manner as Example 3. One hundred grams of the resin prepared in Example 8, 30 grams of triethylamine and 20 grams of methacryloyl chloride were used. The reaction product had a weight of 113.5 grams.

EXAMPLE 10

This example was carried out in the same mamnner as Example 3. One hundrd grams of the resin prepared in Example 8, 62.4 grams of methacryloyl chloride and 90 grams of triethylamine were used.

EXAMPLE 11

Forty-five grams of 2,2'-methylene-bis-(4-ethyl-6-t.butylphenol) and 18.5 grams of triethylamine were dissolved in 100 milliliters of tetrahydrofuran. Fourteen grams of methacryloyl chloride were added below 40° C. over a 10 minute period. After stirring for 30 minutes, the reaction product was washed with water. The volatiles were removed at a reactor temperature below 80° C. under vacuum. The product was recrystallized from petroleum ether. The product had a melting point of 86° C. to 87° C. and was characterized as 2-(2-hydroxy-3-t.butyl-5-ethylbenzyl)-4-ethyl-6-t.butyl phenylmethacrylate. The reaction product had a melting point of 86° C. to 87° C.

EXAMPLE 12

One hundred grams of 2,2'-methylene-bis-4-methyl-6-t.butylphenol) and 60 grams of triethylamine were dissolved in 150 milliliters of tetrahydrofuran. Thirty-one grams of methacryloyl chloride were added over a 10 minute period. The reaction product was stirred at 65° C. to 75° C. for 1 hour and then filtered. The volatiles were removed under a vacuum. The product was recrystallized from petroleum ether yielding nearly pure 2-(2-hydroxy-3-t.butyl-5-methylbenzyl)-4-methyl-6-tert.butyl phenylmethacrylate having a melting point between 141° C. and 142° C.

EXAMPLE 13

Seventy-five grams of 2,2'-thio-bis-(4-methyl-6-t.butylphenol) and 31 grams of triethylamine were dissolved in 150 milliliters of tetrahydrofuran. Twenty-four grams of methacryloyl chloride were added over a 15 minute period at 30° C. The reaction product was stirred for an additional 50 minutes and then washed four times with 150 milliliter portions of water. The reaction product was diluted with 150 milliliters of toluene and filtered. The volatiles were removed at a reactor temperature below 80° C. under vacuum. The product was recrystallized from petroleum ether. The 2-(2-hydroxy-3-t.butyl-5-methylphenylthio)-4-methyl-6-t.butylphenylmethacrylate had a melting point between 171° C. and 172° C.

EXAMPLE 14

Forty-five grams of 2,6-bis-(2-hydroxy-3-t.butyl-5-benzyl)-4-methylphenol and 20 grams of triethylamine were dissolved in 125 milliliters of tetrahydrofuran. Ten grams of methacryloyl chloride were added over a 5 minute period. The reaction product was stirred for 1½ hours at 50° C. and then washed with water. The reaction product was filtered and heated to a reactor temperature of 85° C. under vacuum to remove volatiles.

The aforementioned monomeric antioxidants may be polymerized by well known free radical emulsion polymerization techniques with one or more comonomers that are known to polymerize in free radical initiated polymerization systems. Some adjustments in the polymerization recipe and/or conditions may be necessary to obtain a satisfactory rate of polymer formation, depending on the amount of monomeric antioxidants included and the other monomers involved. Adjustments which may be necessary in the polymerization conditions to improve polymerization rates include increasing the temperature of polymerization and/or increasing the initiator level and/or increasing the level of activator ingredients. Solvents may also be required to obtain adequate solubility of the monomers with each other as well to solubilize other ingredients where required. Some solvents, such as methyl ethyl ketone or isopropyl alcohol, can be used to advantage with the emulsion polymerization system. These adjustments, where necessary, are to counteract the inhibitory effect of the monomeric antioxidant and to insure its solubility in the system.

Examples of free radical initiators that are useful in the practice of this invention are those known as "Redox" initiators, such as appropriate combinations of chelated iron salts, sodium formaldehyde sulfoxylate and organic hydroperoxides such as cumene and paramenthane hydroperoxides. Other initiators such as azoisobutyro-nitrile, benzoyl peroxide, hydrogen peroxide and potassium persulfate may also be used, depending on the particular polymerization recipe.

The monomeric antioxidants used in the practice of this invention have certain chemical characteristics which preclude their use in polymerization processes other than those initiated by free radicals. By "free radical initiated systems" is meant systems wherein free radicals are generated by any of various processes such as thermal decomposition of various persulfate, perborate, peroxide, azo or azonitrile compounds; induced (catalytic or "redox" promoted) decomposition of various persulfate, peroxide or hydroperoxide compounds and generation of free radicals by exposure of the system to high energy radiation such as radiation from a radioactive source or ultraviolet light. Such systems are very well known in the art and are widely used commercially, e.g., in the preparation of SBR, styrene/butadiene copolymers.

The most widely used system for preparation of elastomeric polymers, i.e., polymers prepared from a monomer charge made up of at least 40 weight percent diene, preferably at least 60 weight percent diene, by free radical initiation is the emulsion system. Polymers ranging all the way from liquid, low molecular weight (molecular weights of about 2,000 to 10,000 to polymers of intermediate molecular weight (60,000 to 70,000 and higher), to oil extendable, at least 50 percent soluble, rubbery solid, high molecular weight (100,000 to 500,000 or more) and even highly gelled, less than 50 percent soluble, may be prepared by emulsion polymerization. The monomeric antioxidants of the present invention can be used in such emulsion polymerization systems to produce polymers of the aforementioned type.

The principles of emulsion polymerization are discussed in references such as "Synthetic Rubber" by G. S. Whitby, Editor-in-Chief, John Wiley and Sons, 1954, particularly Chapter 8, and "Emulsion Polymerization" by F. A. Bovey et al, Vol. IX of "High Polymers", Interscience Publishers, Inc., 1955. Some specialized applications of these principles are indicated in U.S. Patents such as U.S. Pat. Nos. 3,080,334; 3,222,334; 3,223,663; 3,468,833 and 3,099,650.

Very effective as free radical polymerization initiators used within the practice of the present invention when used under appropriate conditions, are compounds such as t-butyl hydroperoxide, cumene hydroperoxide, diisopropylbenzene hydroperoxide and paramenthane hydroperoxides, and even hydrogen peroxide. These compounds perform very effectively when used in polymerization recipes containing appropriate levels of supporting ingredients. By "supporting ingredients" is meant those materials often referred to as activators in emulsion, or other systems, where required. U.S. Pat. No. 3,080,334 describes some of these materials at column 5, lines 20–26. Such materials can also be referred to as catalyst activators. The term "Redox Polymerization" is often used where the complete initiation system includes a Redox system, i.e., reducing agents and oxidizing agents in a proportion that yields polymerization initiating species. All of these initiator systems are well known in the art.

Emulsion polymerizations are normally accomplished in the range of 5° C. to 90° C. Though the activated or "Redox" initiated systems are preferred for low temperature polymerizations, they are very effective at high temperatures also, normally requiring appreciably lower quantities of the various ingredients to obtain a desirable polymerization rate.

The free radical sources used in the initiator systems are those customarily used in free radical polymerizations, for example, organic initiators such as azonitriles, azo-derivatives, peroxides, and hydroperoxides and inorganic initiators such as inorganic peroxy compounds. Radiation, e.g., of the ultraviolet and gamma ray type can also be used as a free radical source. Various organic initiators are described by J. Brandrup and E. H. Immergut, Polymer Handbook (John Wiley & Sons), 1965, pages II–3 to II–51.

The polymerizable antioxidants of this invention have been polymerized at the indicated parts per hundred monomer (PHM) to produce nitrile-butadiene rubber (33/67), styrene-butadiene rubber (25/75) and hydroxylated nitrile-butadiene rubber emulsion recipes. The hydroxylated nitrile-butadiene rubber contained a 30/5/65 ratio of acryloyl nitrile/2-hydroxylmethylmethacrylate/butadiene. All polymers were coagulated and then extracted for 48 hours with methanol. Oxygen absorption data are shown in Table I below.

Table I

| Example | PHM | Type Polymer | Hours to Absorb 1% $O_2$ |
|---|---|---|---|
| 4 | 1.5 | Hydroxylated NBR | 119 |
| 5 | 1.5 | Hydroxylated NBR | 82 |
| 6 | 1.5 | Hydroxylated NBR | 76 |
| No Antioxidant | — | Hydroxylated NBR | <10 |

Table I-continued

| Example | PHM | Type Polymer | Hours to Absorb 1% O₂ |
| --- | --- | --- | --- |
| 12 | 1.5 | Hydroxylated NBR | 169 |
| 13 | 1.5 | Hydroxylated NBR | 17 |
| 13 | 1.5 | Hydroxylated NBR | 44 |
| No Antioxidant | — | Hydroxylated NBR | <10 |
| 12 | 1.5 | NBR | 102 |
| 12 | 3.0 | NBR | 107 |
| No Antioxidant | — | NBR | <10 |
| 11 | 1.5 | NBR | 110 |

Other antioxidants which can be made using the processes of this invention were tested by oxygen absorption at 100° C. The sample antioxidants were polymerized in nitrile rubber (NBR) and styrene/butadiene rubber (SBR) recipes at the levels shown, based on 100 parts of the polymer. The data are summarized in Table II. The polymers containing the antioxidant were extracted for 48 hours in methanol to remove any non-bound stabilizer. The oxygen absorptions were carried out by dissolving the extracted antioxidant-containing polymer in benzene to form a cement. The cements were poured onto aluminum foil and dried to form a thin film. The weight of each sample was determined. The aluminum foil with the adhering rubber sample was placed in the oxygen absorption apparatus and the time required to absorb one percent oxygen by weight was recorded. The testing procedure is fully detailed in Industrial and Engineering Chemistry, 43, page 456 (1951) and Industrial and Engineering Chemistry, 45, page 392 (1953).

Table II

| Example* | Parts | Polymer** | 100° C. Hours to 1% O₂ Absorption |
| --- | --- | --- | --- |
| 1 | 1.5 | NBR | 110 |
| 2 | 1.5 | NBR | 222 |
| 2 | 1.5 | SBR | 500 |
| 3 | 1.5 | NBR | 150 |
| 3 | 1.5 | SBR | 431 |
| 4 | 1.5 | SBR | 218 |
| 5 | 1.5 | NBR | 184 |
| 6 | 1.5 | SBR | 420 |
| 7 | 1.5 | SBR | 123 |
| 8 | 1.0 | NBR | 159 |
| 8 | 1.5 | SBR | 11 |
| 9 | 1.0 | NBR | 7.3 |
| 10 | 1.0 | SBR | 42 |

*1. 2-(2-hydroxy-3-tert.butyl-5-ethylbenzyl)-4-ethyl-6-tert.butyl phenyl methacrylate
2. (3,5-ditert.butyl-4-hydroxy benzyl) phenyl methacrylate
3. 2-(3,5-ditert.butyl-4-hydroxy benzyl)-4-methyl phenyl methacrylate
4. 2-(2-hydroxy-3-tert.butyl-5-methylbenzyl)-4-methyl-6-tert.butyl phenyl acrylate
5. 1:1 reaction product of the material produced in Example 2 and acryloyl chloride
6. 2-(3,5-ditert.butyl-4-hydroxylbenzyl)-4-methyl phenyl acrylate
7. Reaction product prepared as described in Example 3
8. 2-(2-hydroxy-3-tert.butyl-5-methylbenzyl)-4-methyl-6-tert.butyl phenyl methacrylate
9. 2-(2-hydroxy-3-tert.butyl-5-methyl phenylthio)-4-methyl-6-tert.butylphenyl methacrylate
10. Reaction product produced as described in Example 14. Expected major product is 2,6-bis-(2-hydroxy-3-tert.butyl-5-methylbenzyl)-4-methyl phenyl methacrylate
** NBR — nitrile rubber
SBR — styrene/butadiene rubber While certain representative embodiments and details have been shown for the purpose of illustrating the invention, it will be apparent to those skilled in this art that various changes and modifications can be made herein without departing from the spirit or the scope of this invention.

I claim:

1. A process of preparing an antioxidant polymeric composition comprising polymerizing in a free radical, emulsion polymerization system a monomer system containing at least one compound comprising the reaction product of a polyphenolic compound having the formula

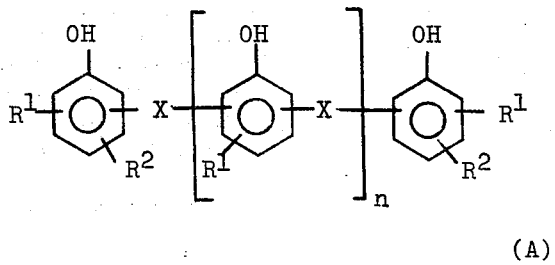

(A)

wherein $R^1$ and $R^2$ are the same or different radicals selected from the group consisting of hydrogen, alkyl radicals containing from 1 to 16 carbon atoms, cycloalkyl radicals containing from 5 to 9 carbon atoms aralkyl radicals containing from 7 to 12 carbon atoms and substituted and unsubstituted aryl radicals containing from 6 to 12 carbon atoms, X is the same or different radical selected from the group consisting of (1) cyclic dienes with nonadjacent carbon to carbon double bonds within the ring structure having from 5 to 20 carbon atoms from which the divalent species are prepared and (2) bivalent species selected from the group consisting of —S—,

—O—, —CH₂— and —S—S— and wherein $n$ is selected from the group consisting of 0 and real numbers from 1 to 5 with an ester forming compound of the general formula

(B)

wherein $R^3$ is selected from the group consisting of hydrogen and alkyl radicals having from 1 to 4 carbon atoms, $R^4$ is selected from the group consisting of hydrogen, alkyl radicals having from 1 to 4 carbon atoms, aralkyl radicals having from 7 to 12 carbon atoms, cycloalkyl radicals having from 5 to 8 carbon atoms and substituted or unsubstituted aryl radicals having from 6 to 12 carbon atoms and wherein A is selected from the group consisting of chlorine, iodine and bromine, and wherein the monomer system contains at least 40 parts by weight of a diene monomer per 100 parts by weight of the total monomer in the monomer system.

2. A polymer prepared according to the process of claim 1.

3. The process according to claim 1 wherein $R^1$ is an alkyl radical having from 1 to 2 carbon atoms and is para to a phenolic hydroxyl group.

4. The process according to claim 1 above wherein the polyphenolic compounds are treated with from one mol to 0.1 mol of ester forming compound per functional hydroxyl group, more preferably at least one functional hydroxyl group per polyphenolic molecule esterified.

5. The process according to claim 1 wherein the polyphenolic compounds are selected from the group consisting of 2,6-bis(2-hydroxy-3-tert.butyl-5-methylbenzyl)-4-methylphenol; 2,2'-methylene-bis(4-methyl-6-tert.butylphenol); 2,2'-methylene-bis(4-ethyl-6-tert.butylphenol); 2,2-thio-bis((4-methyl-6-tert.butylphenol); 2-(3,5-ditert.butyl-4-hydroxybezyl)-4-methylphenol; 4-(3,5-ditert.butyl-4-hydroxybenzyl)phenol; 2-(3,5-ditert.butyl-4-hydroxybenzyl)phenol; 2-(3,5-ditert.butyl-4-hydroxybenzyl)-5-methylphenol and 2,6-bis-(2-hydroxy-3-tert.butyl-5-ethylbenzyl)-4-ethylphenol.

6. The process according to claim 1 wherein the cyclic dienes are selected from the group consisting of 1,5-cyclooctadiene; cyclopentadiene; bicyclo[2.2.1]-2,5-heptadiene; dicyclopentadiene; pentacyclo[8.2.1.1$^{4,7}$.0$^{2,9}$.0$^{3,8}$]-tetradeca-5,11-diene, and 1,5,9-cyclododecadiene.

7. The process according to claim 1 wherein the ester forming compounds are selected from the group consisting of acryloyl cloride and methacryloyl chloride.

8. The process of claim 1 wherein the number of ester groups reacting with the polyphenolic reactant is not more than $n + 1.5$ and not less than $n - 0.75$.

9. The process of claim 1 wherein X is a cyclic diene according to claim 1 or a bivalent species selected from the group consisting of

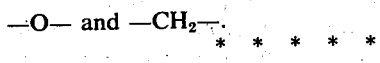

* * * * *